United States Patent [19]

Schaap

[11] Patent Number: 4,983,779
[45] Date of Patent: * Jan. 8, 1991

[54] PROCESS FOR THE PREPARATION OF VINYL ETHERS

[75] Inventor: Arthur P. Schaap, Detroit, Mich.

[73] Assignee: The Board of Governors of Wayne State University, Detroit, Mich.

[*] Notice: The portion of the term of this patent subsequent to Aug. 15, 2006 has been disclaimed.

[21] Appl. No.: 450,459

[22] Filed: Dec. 14, 1989

Related U.S. Application Data

[63] Continuation-in-part of Ser. No. 289,837, Dec. 27, 1988, which is a continuation-in-part of Ser. No. 887,139, Jul. 17, 1986.

[51] Int. Cl.$^5$ ............................................. C07C 41/18
[52] U.S. Cl. ..................... 568/660; 549/214; 549/221; 549/408; 549/410; 549/414; 549/462; 549/470; 549/510; 549/511; 556/446; 558/37; 558/194; 560/108; 560/140
[58] Field of Search ............... 549/408, 462, 410, 470; 556/446; 558/37, 194; 560/108, 140; 568/660; 536/4.1, 18.1

[56] References Cited

U.S. PATENT DOCUMENTS 4,857,652  8/1985  Schaap ................................. 549/510

OTHER PUBLICATIONS

McMurry, Chemical Review, 89 (1989) 1513-1524.
McMurry et al., Acc. Chem. Res. 16, 405-411 (1983).
Dams et al., J. Org. Chem. 47, 248-259 (1982).
McMurry et al., J. Org. Chem. 43, 3255-3266 (1978).
Mukaiyama et al., Chem. Lett. 1041-1044 (1973).
McMurry et al., JACS 96, 4708-4709 (1974).
Tyrlik et al., Bull. Soc. Chim. Fr. 6, No. 2147-2148 (1973).

*Primary Examiner*—Richard L. Raymond
*Attorney, Agent, or Firm*—Ian C. McLeod

[57] ABSTRACT

An improved process for the preparation of vinyl ethers by the coupling reaction of an ester of the formula

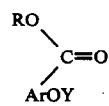

with a carbonyl containing compound of the formula

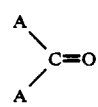

wherein A and R are passive organic groups and OY is a hydroxyl group or OP where P is a protecting group is described. The ester and the carbonyl containing compound are reacted in an organic solvent with a titanium salt, a metallic reducing agent and an amine base to provide the vinyl ether. The reaction is safe and produces high yields. The vinyl ethers are useful for producing dioxetanes which produce light upon triggering.

16 Claims, No Drawings

PROCESS FOR THE PREPARATION OF VINYL ETHERS

CROSS-REFERENCE TO RELATED APPLICATION

This application is a continuation-in-part of my pending U.S. patent application Ser. No. 289,837, filed Dec. 27, 1988 which is a continuation-in-part of my pending U.S. patent application Ser. No. 887,139, filed July 17, 1986.

BACKGROUND OF THE INVENTION

The present invention relates to an improved process for the preparation of vinyl ethers by coupling of a ketone with an aryl ester bearing a hydroxyl (OH) group or an OP group wherein P is a typical protecting group for an OH group. In particular, the present invention relates to a coupling reaction which is conducted in an organic solvent, preferably an ether, using a titanium salt, preferably $TiCl_3$ or $TiCl_4$, and a metallic reducing agent, preferably zinc metal, in the presence of an amine, preferably triethylamine.

PRIOR ART

The use of various reducing agents such as lithium aluminum hydride (LAH), Zn-Cu couple and Li, K, Zn or Mg metals in combination with $TiCl_3$ or $TiCl_4$ to synthesize alkyl and aryl substituted alkenes by a coupling of ketones has been described in the literature. These reactions are described by McMurry et al. Acc. Chem. Res. 16, 405–411 (1983); Dams et al, J. Org. Chem. 47, 248–259 (1982); McMurry et al, J. Org. Chem. 43, 3255–3266 (1978); Mukaiyama et al, Chem. Lett. 1041–1044 (1973); McMurry et al JACS 96, 4708–4709 (1974); Tyrlik et al, Bull. Soc. Chim. Fr. 6, No. 2147–2148 (1973). My U.S. patent application Ser. No. 887,139 specifically shows the use of lithium aluminum hydride as a reducing agent for the previously unknown preparation of vinyl ethers. This process can be difficult to control and, therefore, somewhat dangerous in large scale reactions.

The vinyl ethers are used to produce triggerable 1,2-dioxetanes which produce light. These compounds are particularly useful in various biological assays for detecting materials.

OBJECTS

It is therefore an object of the present invention to provide an improved process which uses an ester and a ketone in a coupling reaction to produce a vinyl ether bearing an aryl group with either a hydroxyl (OH) group or an OP group wherein P is a protecting group. These and other objects will become increasingly apparent by reference to the following description.

GENERAL DESCRIPTION

The present invention relates to a process for producing a vinyl ether of the formula

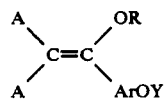

wherein A and R are passive organic groups, wherein ArOY is an aryl group having an aryl ring substituted with OY as a substituent selected from the group consisting of hydroxyl and OP, wherein P is a protecting group which comprises:

reacting a carbonyl containing compound of the formula:

with an ester compound of the formula:

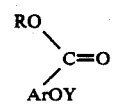

an organic solvent in the presence of a metallic reducing agent such as zinc metal, a titanium salt and an amine base to produce the vinyl ether.

Thus A and R can be any essentially passive organic group such as for instance alkyl, aryl, or polycyclic alkyl.

Further, the present invention relates to a process for producing a vinyl ether of the formula

wherein $R_1$ is selected from alkyl, aryl, and aralkyl containing 1 to 20 carbon atoms and optionally including oxygen, sulfur, nitrogen, phosphorus and halogens (chlorine, bromine, iodine), $R_2$ is selected from aryl, biaryl and fused ring polycyclic aryl groups which can be substituted or unsubstituted, wherein $R_1$ and $R_2$ can be linked together by a member selected from carbon, oxygen and nitrogen containing groups and $R_3C$— is selected from polycyclic alkyl groups containing 6 to 30 carbon atoms, wherein OY is a substituent selected from hydroxyl and OP and wherein P is a protecting group which comprises:

reacting a carbonyl containing compound of the formula:

with an ester compound of the formula:

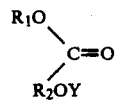

in an organic solvent in the presence of a metallic reducing agent such as zinc metal, a titanium salt, and an amine base to produce the vinyl ether.

Preferably the metallic reducing agent and titanium salt are provided with the amine base at temperatures between about −25 and +25° C. The amine is added slowly to the reducing agent and titanium salt in a reaction mixture to prevent the exothermic reaction from becoming uncontrollable. The ketone and ester are added in a solvent and the reaction conducted between about 25° and 150° C. The vinyl ether is then separated from the reaction mixture using conventional techniques.

The metallic reducing agent is preferably essentially pure zinc. Zinc can be used as the metal alone or in admixture with other metals such as copper. Other pure metals such as Li, K, and Mg can be used. Zinc alone is preferred. The metallic reducing agent is preferably finely divided.

The titanium salt is preferably in the form of a chloride. Either titanium trichloride or titanium tetrachloride can be used.

The amine can be triethylamine which is preferred. Other amine acid acceptors which do not interfere with the reaction to form the vinyl ether can be used. Such amine bases are well known to those skilled in the art.

The organic solvent is preferably an ether. The most preferred solvent is tetrahyrofuran. Other solvents are, for instance, dimethoxyethane or dioxane.

The preferred vinyl ethers for instance are made from 2-adamantanone and esters as shown below, where R is, for instance, CH$_3$(Me), CH$_2$CH$_3$, CH$_2$CH$_2$Cl, CH$_2$CH$_2$CH$_2$Cl, (CH$_2$)$_{15}$CH$_3$, CH$_2$Ph, or Ph.

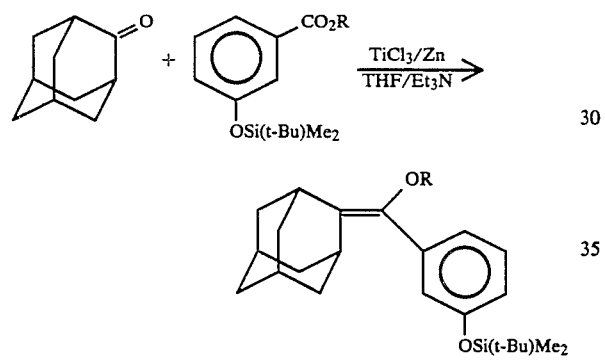

Additional preferred vinyl ethers are made from 2-adamantanone and esters of 3-hydroxybenzoate as shown below, where R is, for instance, CH$_3$(Me), CH$_2$CH$_3$, CH$_2$CH$_2$Cl, CH$_2$CH$_2$CH$_2$Cl, (CH$_2$)$_{15}$CH$_3$, CH$_2$Ph, or Ph.

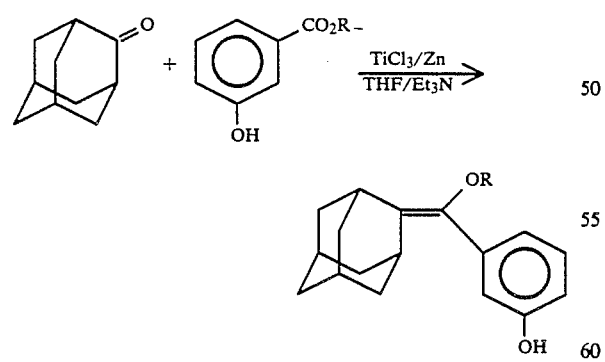

The preferred vinyl ethers are also made by the following process from 2-adamantanone and the corresponding methyl 3-silyloxy or 3-hydroxybenzoate where Y=H, Si(t-Bu)Me$_2$, Si(t-Bu)Ph$_2$, or SiPh$_3$ and where Ph is phenyl, Bu is t-butyl and Me is methyl. Other protecting groups well known in the literature can also be used.

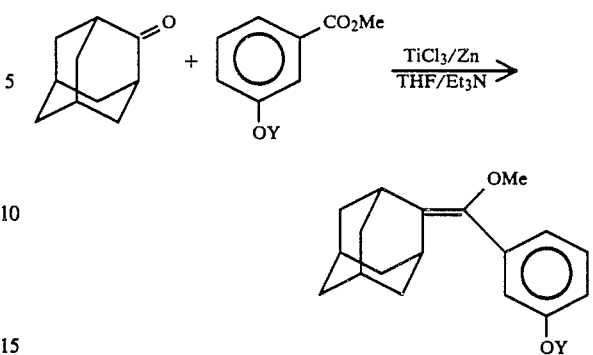

The following vinyl ethers are made by this general process from 2-adamantanone and the corresponding esters including lactones, where Y is hydrogen or a protecting group.

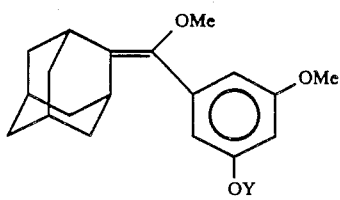

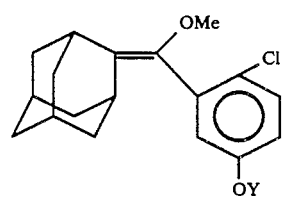

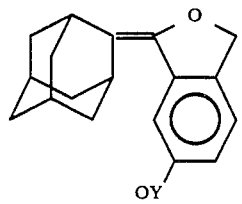

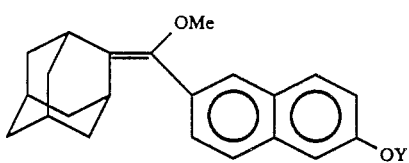

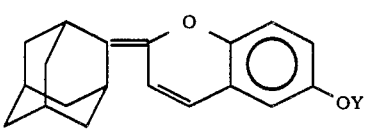

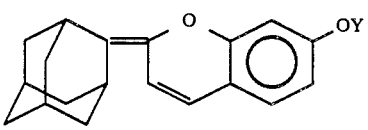

The following vinyl ether is made by this general process from the ketone, bicyclo[3.3.1]nonan-9-one, and methyl 3-tert-butyldimethylsilyloxybenzoate.

stituted dioxetane as described in U.S. application Ser. No. 887,139.

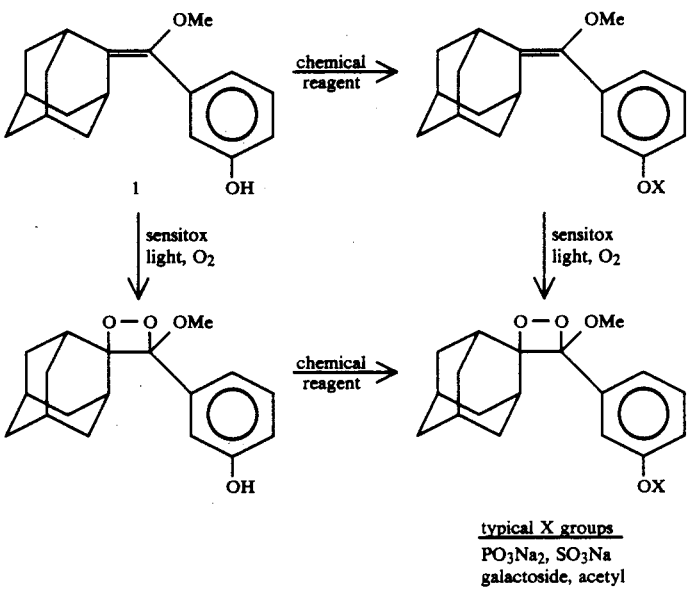

typical X groups
PO$_3$Na$_2$, SO$_3$Na
galactoside, acetyl

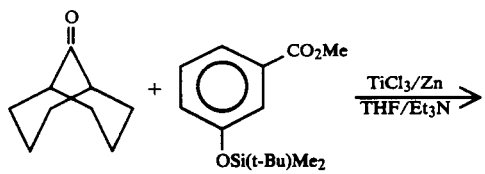

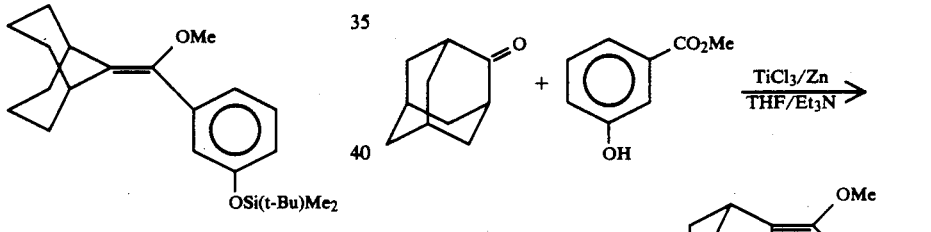

The hydroxyl vinyl ether is prepared either by direct reaction of a ketone and a hydroxy ester or by reaction of a ketone and ester bearing an OY group with subsequent conversion of OY to OH by removal of the protecting group P in a known manner. The hydroxyl-substituted vinyl ethers such as the preferred example, [(3-hydroxyphenyl)methoxymethylene]adamantane (1) shown below, are converted to other derivatives by standard chemical processes well known to those skilled in the art of organic synthesis. Such derivatives are, for instance, esters of inorganic oxy acids or their salts (e.g. phosphates, sulfates) oxygen-pyranosides (e.g., beta-D-galactosides) and aryl or alkyl carboxyl esters. The vinyl ethers are then converted to dioxetanes, as shown below, which are triggerable by corresponding enzymes, (phosphatase, sulfatase, beta-D-galactosidase, esterase and the like) to produce light in biological assays. The dioxetanes can also be chemically triggered.

Thus the vinyl ether can be directly photooxidized in the presence of a sensitizer, light and oxygen to yield the desired dioxetane. Alternatively, the hydroxy vinyl ether, such as 1 shown below, is photooxidized to give the hydroxy substituted dioxetane and it is subsequently treated with chemical reagents to form the X-sub-

SPECIFIC DESCRIPTION

The following Examples show the preferred processes of the present invention for producing the vinyl ethers.

EXAMPLE 1

[((3-Hydroxyphenyl)methoxymethylene]adamantane (1). To a four-necked round-bottom flask equipped with a refluxing condenser and mechanical stirrer was added 1.5 L of dry THF under argon. Titanium trichloride (TiCl$_3$, 200 g, 1.29 mol) was then added to the flask with stirring. After 15 minutes of stirring, powdered zinc (130 g, 2.0 mol) was added in portions and the flask was heated in hot water for 25 minutes. The reaction flask was then cooled an ice-salt bath and the temperature of the mixture maintained at 5° to 7° C. Triethylamine (2.0 mL) was added to the suspension with caution (the reaction is extremely exothermic). The reaction started in approximately 5 to 10 minutes. After the reaction subsided, an additional amount of triethylamine (200 mL) was added and the mixture heated under reflux for 3 hours. After this period, a solution of methyl 3-hydroxybenzoate (100 g, 0.66 mol) and 2-adamantanone (60.0 g, 0.40 mol) in 400 mL of dry THF was added dropwise to the refluxing mixture over 5 hours. The reaction mixture was then cooled to room temperature and was diluted with hexane (4 L) and the stirring continued. The suspended solids were then allowed to settle and the organic layer decanted. The black solid was washed with diethyl ether (2 L), followed by 1 L of water and the organic layer was removed. The aqueous layer was washed a second time with 2×2 L of ether. The combined ether layers were then gravity filtered and the resulting solution was dried over anhydrous magnesium sulfate. Evaporation of the solvent under reduced pressure and chromatography over silica gel with 25% ethyl acetate/hexane gave 55.0 g of 1 as white crystals: mp 133.4° C.; $^1$H NMR (CDCl$_3$) δ 1.64–1.96 (m, 12H), 2.65 (s, 1H), 3.24 (s. 1H), 3.32 (s. 3H), 5.25 (s, 1H, OH exchange with D$_2$O) 6.76–6.92 (m, 3H) 7.26 (t, 1H, 7.8 Hz); $^{13}$C NMR (CDCl$_3$) δ 28.45, 30.36, 32.36, 37.30, 39.18, 39.33, 57.82, 114.60, 116.16, 122.19, 129.24, 137.24, 155.62; MS m/e (rel. intensity) 271 (M+1, 20), 270 (M$^+$, 100), 253 (7.3), 213 (35.1), 121 (41.7), 93 (9.4); Exact mass: calcd. 270.1619, found 270.1616; Anal Calcd. for C$_{18}$H$_{22}$O: C, 80.00; H, 8.15. Found: C, 79.85; H 8.34.

This procedure has also been conducted using TiCl$_4$ and Zn and found to give alkene 1 in comparable yields.

EXAMPLE 2

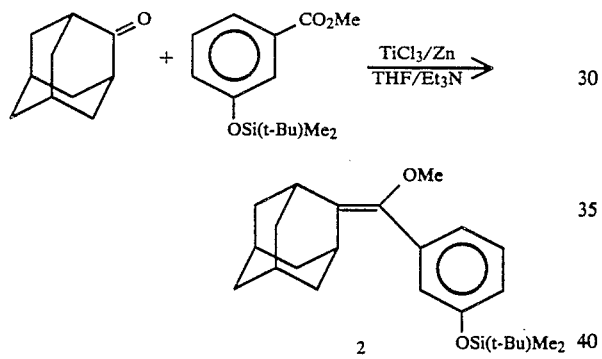

[(3-tert-Butyldimethylsilyloxyphenyl)methoxymethylene]adamantane (2). To a four-necked round-bottom flask equipped with a refluxing condenser and mechanical stirrer was added 1.5 L of dry THF under argon. Titanium trichloride (TiCl$_3$, 200 g, 1.29 mol) was then added to the flask with stirring. After 15 minutes of stirring, powdered zinc (130 g, 2.0 mol) was added in portions and the flask was heated in hot water for 25 minutes. The reaction flask was then cooled in an ice-salt bath and the temperature of the mixture maintained at 5° to 7° C. Triethylamine (2.0 mL) was added to the suspension with caution (the reaction is extremely exothermic). The reaction started in approximately 5 to 10 minutes. After the reaction subsided, an additional amount of triethylamine (200 mL) was added and the mixture heated under reflux for 3 hours. After this period, a solution of methyl 3-tert-butyldimethylsiloxybenzoate (100 g, 0.37 mol) and 2-adamantanone (85.0 g, 0.57 mol) in 400 mL of dry THF was added dropwise to the refluxing mixture over 5 hours. The reaction mixture was then cooled to room temperature and was diluted with hexane (4 L) and the stirring continued. The suspended solids were then allowed to settle and the organic layer decanted. The black solid was washed with diethyl ether (2×1 L). Hexane (1 L) was added to the black material, followed by 1 L of water and the organic layer was removed. The aqueous layer was washed a second time with 1.5 L of hexane. The combined hexane and ether layers were then gravity filtered and the resulting solution was dried over anhydrous magnesium sulfate. Evaporation of the solvent under reduced pressure and chromatography over silica gel with 5% ethyl acetate/hexane gave 117 g (81% yield) of 2 as a clear oil.

This procedure has also been conducted using TiCl$_4$ and Zn and found to give alkene 2 in comparable yields. $^1$H and $^{13}$C NMR spectra of 2 were found to be identical to those of the same alkene prepared by the process of U.S. patent application Ser. No. 887,139, filed July 17, 1986 which utilizes lithium aluminum hydride instead of zinc.

It is intended that the foregoing description be only illustrative of the present invention and that the present invention be limited only by the hereinafter appended claims.

I claim:

1. A process for producing a compound of the formula

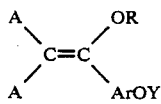

wherein A and R are passive organic groups, wherein ArOY is an aryl group having an aryl ring substituted with OY as a substituent selected from hydroxyl and OP, wherein P is a protecting group which comprises:
   reacting a carbonyl containing compound of the formula:

with an ester compound of the formula:

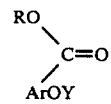

group in an organic solvent in the presence of a metallic reducing agent, a titanium salt and an amine base to produce the vinyl ether.

2. The process of claim 1 wherein the metallic reducing agent is zinc.

3. The process of claim 2 wherein the titanium salt is selected from the group consisting of titanium trichloride and titanium tetrachloride.

4. The process of claim 3 wherein the amine base is triethylamine and the organic solvent is tetrahydrofuran.

5. The process of claim 1 wherein OY is selected from the group consisting of trialkylsilyoxy, dialkylarylsilyoxy, diarylalkylsilyloxy and triarylsilyoxy.

6. The process of claim 1 where OY is a hydroxyl group.

7. A process for producing a vinyl ether of the formula

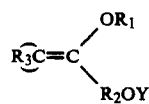

wherein R₁ is selected from the group consisting of alkyl, aryl and aralkyl containing 1 to 20 carbon atoms and optionally including oxygen, sulfur, nitrogen, phosphorus 8. The process of claim 7 wherein the metallic reducing agent is zinc.

9. The process of claim 8 wherein the titanium salt is selected from the group consisting of titanium trichloride and titanium tetrachlroide.

10. The process of claim 9 wherein the amine base is triethylamine and the organic solvent is tetrahydrofuran.

11. The process of claim 7 wherein OY is selected from the group consisting of trialkylsilyoxy, dialkylarylsilyoxy, diarylalkylsilyloxy and triarylsilyoxy.

12. The process of claim 7 wherein OY is a hydroxyl group.

13. The process of claim 7 wherein in addition the Y in the vinyl ether is replaced subsequently with another group to provide an OX group selected from the group consisting of inorganic oxy acid salt, phosphate salt, oxygen-pyranoside, aryl and alkyl carboxyl esters, and halogens, R₂ is selected from aryl, biaryl and fused ring polycyclic aryl groups which can be substituted or unsubstituted, wherein R₁ and R₂ can be linked together by a member selected from carbon, oxygen or nitrogen containing groups and R₃C— is selected from polycyclic alkyl groups containing 6 to 30 carbon atoms, wherein OY is a substituent selected from hydroxyl and OP and wherein P is a protecting group which comprises:

reacting a carbonyl containing compound of the formula:

with an ester compound of the formula:

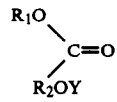

in an organic solvent in the presence of a metallic reducing agent, a titanium metal salt, and an amine base to produce the vinyl ether.

14. The process of claim 1 wherein the amine is added slowly to the metallic reducing agent and titanium salt in admixture prior to reacting the carbonyl containing compound and the ester compound.

15. The process of claim 14 wherein the titanium salt is a chloride.

16. The process of claim 15 wherein the metallic reducing agent is finely divided.

* * * * *

UNITED STATES PATENT AND TRADEMARK OFFICE
CERTIFICATE OF CORRECTION

PATENT NO. : 4,983,779
DATED : January 8, 1991
INVENTOR(S) : Arthur P. Schaap

It is certified that error appears in the above—identified patent and that said Letters Patent is hereby corrected as shown below:

Column 3, line 18, "tetrahyrofuran" should be --tetrahydrofuran--.

Column 6, line 58, after "cooled", --in-- should be inserted--.

Column 7, line 14 "(S. 1H)" and "(S. 3H)" should be --S, 1H)-- and --(S, 3H)--, respectively.

Column 9, line 10, Claim 7, the following should be inserted:
--and halogens, $R_2$ is selected from aryl, biaryl and fused ring polycyclic aryl groups which can be substituted or unsubstituted, wherein $R_1$ and $R_2$ can be linked together by a member selected from carbon, oxygen or nitrogen containing groups and $R_3C-$ is selected from polycyclic alkyl groups containing 6 to 30 carbon atoms, wherein OY is a substituent selected from hydroxyl and OP and wherein P is a protecting group which comprises:

UNITED STATES PATENT AND TRADEMARK OFFICE
CERTIFICATE OF CORRECTION

PATENT NO. : 4,983,779
DATED : January 8, 1991
INVENTOR(S) : Arthur P. Schaap

It is certified that error appears in the above—identified patent and that said Letters Patent is hereby corrected as shown below:

reacting a carbonyl containing compound of the formula:

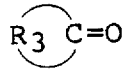

with an ester compound of the formula:

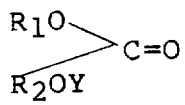

in an organic solvent in the presence of a metallic reducing agent, a titanium metal salt, and an amine base to produce the vinyl ether.--.

Column 9, line 15, Claim 9, "tetrachlroide" should be --tetrachloride--.

Column 9, line 28, Claim 13, delete ", and" at the end of the line.

Column 9, delete line 29 to Column 10, line 22.

Signed and Sealed this

Seventh Day of July, 1992

Attest:

DOUGLAS B. COMER

Attesting Officer      Acting Commissioner of Patents and Trademarks